US006955776B1

United States Patent
Feenstra

(10) Patent No.: US 6,955,776 B1
(45) Date of Patent: Oct. 18, 2005

(54) METHOD FOR MAKING A DENTAL ELEMENT

(75) Inventor: Frits Kornelis Feenstra, Pijnacker (NL)

(73) Assignee: Nederlandse Organisatie voor toegepast-natuurwetenschappelijk Onderzoek TNO, Delft (NL)

( * ) Notice: Subject to any disclaimer, the term of this patent is extended or adjusted under 35 U.S.C. 154(b) by 248 days.

(21) Appl. No.: 10/069,329

(22) PCT Filed: Aug. 24, 2000

(86) PCT No.: PCT/NL00/00585

§ 371 (c)(1),
(2), (4) Date: Apr. 30, 2002

(87) PCT Pub. No.: WO01/13814

PCT Pub. Date: Mar. 1, 2001

(30) Foreign Application Priority Data

Aug. 24, 1999 (NL) .................................. 1012897

(51) Int. Cl.⁷ ............................................. A61C 13/00
(52) U.S. Cl. ...................... 264/16; 264/460; 264/434; 264/112
(58) Field of Search ............................ 264/16, 17, 19, 264/20, 109, 112, 460, 462, 434; 425/375, 425/174.4; 427/2.1, 2.29, 180

(56) References Cited

U.S. PATENT DOCUMENTS

| 4,705,762 | A | * | 11/1987 | Ota et al. |
| 5,204,055 | A | * | 4/1993 | Sachs et al. |
| 5,641,434 | A | * | 6/1997 | Yamada et al. |
| 5,690,490 | A | | 11/1997 | Cannon et al. |
| 5,823,778 | A | | 10/1998 | Schmitt et al. |
| 5,902,441 | A | | 5/1999 | Bredt et al. |
| 6,322,728 | B1 | * | 11/2001 | Brodkin et al. |
| 2004/0024470 | A1 | * | 2/2004 | Giordano et al. ......... 623/23.51 |

FOREIGN PATENT DOCUMENTS

| EP | 0 431 924 A3 | 11/1991 |
| EP | 0 431 924 A2 | 12/1991 |
| WO | WO 91/03988 | 4/1991 |
| WO | WO 98/51747 | 11/1998 |

* cited by examiner

Primary Examiner—Steven P. Griffin
Assistant Examiner—Carlos Lopez
(74) Attorney, Agent, or Firm—Lucas & Mercanti, LLP

(57) ABSTRACT

The present invention relates to a method for fabricating a functional dental element, such as a crown. According to the invention, use is made of a three-dimensional printing technique. The major advantages of the invention are that no mold is needed anymore, which entails a considerable saving of costs, that a great accuracy is achieved, and that the element can be made of different materials.

20 Claims, No Drawings

METHOD FOR MAKING A DENTAL ELEMENT

BACKGROUND OF THE INVENTION (1) Field of the Invention

The invention relates to a method for making a functional dental element and to a dental element obtainable by such method.

(2) Description of Related Art

Dental elements, such as crowns, are used in clinical practice mainly for replacing or correcting dental structures. This can involve partly or wholly lost teeth or molars. To date, materials for such elements have been examined in particular for technological/physical and chemical properties. Currently, in addition, the biological aspect plays an increasing role.

Dental elements can be fabricated from different materials. Examples include polymers, metals, composites, combinations of porcelain and metal, porcelain and other ceramic materials. Glass and ceramic materials form an ideal group of materials for dental elements, because they are hard, have a high wear resistance, are chemically inert in many media (biocompatibility), and can be simply formed into an aesthetic dental element. A broad application of these materials, however, is impeded by the inherent brittleness which is often the result of limitations in the fabricating process and of the material choice. Recent developments have led to different ceramic systems, such as sintered ceramic, glass-infiltrated ceramic and glass-ceramic of various compositions, which are less brittle.

The fabrication of dental elements in practice is a complex and time consuming affair. The products involved are fabricated on an individual basis since the exact form of the element is different for every tooth or molar in every individual. Conventional techniques that have been used often utilize a mold. Since this mold can typically be used only once, it will be clear that these techniques are very costly.

In the past, techniques have been proposed which supposedly enable simplification of the fabricating process of dental elements. Thus, Abe et al., in Int. J. Japan Soc. Prec. Eng., vol. 30, no. 3, 1996, pp. 278–279, have proposed to carry out a selective laser sintering (SLS) with titanium. This technique, however, often gives rise to shrinkage. Also, microcracks may be formed, which renders the technique unsuitable for the fabrication of functional dental elements. In European patent application 0 311 214 it has been proposed to make a crown by milling. Milling does not provide the possibility of making colored elements. Moreover, the choice of suitable materials that can be processed by milling is limited. As noted, ceramic materials form an ideal group of materials for fabricating dental elements, because they are hard, highly wear-resistant and inert under many conditions.

U.S. Pat. No. 5,690,490 describes a method for fabricating a concept model for a dental element by so-called pinhead molding. The method concerns the use of a kind of matrix printing technique, whereby material is sprayed on. The printer is controlled with a CAD/CAM program. The data which this program utilizes have been obtained from a laser scan of the tooth or the molar to be replaced.

In U.S. Pat. No. 5,823,778, a method is described for the fabrication of a dental element whereby an impression of the teeth of a patient is obtained, which is subsequently used as a mold to make a copy of a dental element. This element is broken down in layers and each layer is scanned to obtain a three-dimensional computer model of the dental element.

SUMMARY OF THE INVENTION

One object of the present invention is to provide a technique whereby functional dental elements can be fabricated in a flexible and efficient manner. Another object is for the technique not to utilize a mold, and to enable making dental elements of polymeric, metallic or ceramic material, or of combinations thereof.

Surprisingly, it has presently been found that the stated objects are achieved by fabricating a dental element utilizing a three-dimensional printing technique.

Three-dimensional printing techniques are known per se, and described inter alia in European patent application 0 431 924, U.S. Pat. No. 5,902,441 and international patent applications 94/19112, 97/26302 and 98/51747. For a description of the details of the technique, reference is made to the documents mentioned, which are therefore to be understood to be inserted herein.

The method according to the invention is in principle suitable for fabricating all types of dental elements. Examples include crowns (front and lateral teeth), inlays, overlays, onlays, partial crowns, fixations and veneers.

DETAILED DESCRIPTION OF THE INVENTION

Preferably, in a patient in whom a dental element is to be replaced/placed, it is first accurately measured what shape the element is to have. Often, if possible, the starting point will be the shape of the tooth or molar, or the portion thereof that is to be replaced. It is preferred that measurement can take place in a manner which causes the patient as little inconvenience as possible. Particularly suitable techniques for measuring the shape for the dental element make use of optical scan techniques, in particular the use of lasers. In electronic form, data about the desired shape and dimensions are thereby obtained, which can be directly visualized in a computer. The electronic data about the shape and dimensions of the dental element are preferably used by a computer to control the execution of the three-dimensional printing technique. Another suitable method for measuring is by the CEREC-technique, Sirona Dental Systems GmbH, Bensheim, Germany.

In the three-dimensional printing technique, a suitable material is applied successively in layers, while specific steps are taken to ensure that each layer adheres to the preceding layer only at particular desired points. These specific steps are determined by the desired shape of the dental element and preferably controlled by the above-mentioned electronic data.

According to the invention, in the specific steps mentioned, use is made of a binder. This binder is applied to a preceding layer only at the desired specific points. When to the binder a layer of, for instance, ceramic material from which the dental element is to be shaped, is applied, this will adhere only to the desired points. The non-adhering powder, which, accordingly, does not come into contact with the binder, can be simply removed.

The binder is preferably applied to the desired points by means of a print head, controlled by the computer on the basis of the data obtained upon measurement. Thereafter, a powder of the material that has been selected for the fabrication of the dental element is applied.

It is also possible to work upside down and to provide a layer of binder on the bottom side of a plate and subsequently to dip the binder in the powder. In this last variant, in a simple manner, different kids of powder can be used for different layers. In both cases, the powder will bind only at points where binder has been applied. By repeating these steps sufficiently often, eventually the desired shape of the dental element is obtained. Finally, the binder can be removed by sintering.

According to an alternative to this method, first loose powder is laid in a powder bed, and thereafter binder is applied locally to obtain binding at the desired points. So, in fact, binder and powder can be applied in any sequential order.

The substrate on which work is done can be formed by a few layers of loose powder, so that the dental element to be formed can be readily detached from the substrate. In sintering, preferably a non-adhering substrate, for instance a metal plate, is used.

By virtue of the accuracy of the data that can be obtained by measuring with the aid of a laser technique, and by virtue of the accuracy with which a computer, on the basis of those data, can control a print head, the desired shape and dimensions of the dental element can be obtained in a highly accurate manner. While in the old-fashioned techniques it was necessary to additionally shape a dental element several times after it had been formed in a mold, in the method according to the invention it normally suffices to carry out additional shaping a single time. Depending on the material that has been selected for the dental element, this additional shaping can be carried out by grinding, filing, polishing, sanding, blatting or by using a ball bed (a vibrating box containing abrasive balls).

The binder that is used in a method according to the invention should be soluble in a suitable solvent to a solution having a viscosity of 1–40 mPas, preferably about 3 mPas, and a loading degree of 3–10 wt. %. Thus the binder preferably has a relatively low molecular weight. Examples of suitable binders are colloidal silica, polyvinyl acetate (PVA), starch adhesives, acrylates, polyvinyl alcohol, polyethylene oxide (PEO), ethylenevinyl acetate (EVA) and derivatives thereof.

In the binder, often a colorant will be used. Suitable colorants are normally based on inorganic pigments having a high content of $SiO_2$, which renders them heat-resistant. These substances are known per se and commercially available, for instance, from Carmen, Esprident GmbH, Ispringen, Germany, or VITA Zahnfabrik H. Rauter GmbH & co., Bad Zäckingen, Germany. Preferably, one or more of the following colorants are used: SiO, CoO, ZnO, $Cr_2O_8$, $TiO_2$, $Sb_2O_3$, $Fe_2O_3$ and $MnO_2$. Depending on the desired dental color, colorants are preferably used in amounts of up to 10% by weight, based on the weight of the powder. It is a particular advantage of the invention that at different points in the dental element, different colors can be used, if desired with a transparent outer layer, yielding a natural optical depth action. By virtue of these and other advantages, a dental element resembles a real tooth or molar extremely faithfully.

As noted, this binder can be applied to a suitable substrate with a print head. The print head is controlled by a computer on the basis of the data which have been obtained through prior measurements on the patient for the purpose of the dental element. Examples of suitable print heads are, for instance, inkjet heads of the continuous or of the drop-on-demand type. The print head preferably has a spray nozzle of a diameter between 10 and 100 $\mu$m, more preferably between 25 and 75 $\mu$m and a length between 50 and 150 $\mu$m.

The powder that is used is selected on the basis of the material of which the dental element is eventually to be made. The powder can be used both in dry form and in dispersed form (slurry). Dispersions are preferably prepared in water or an aqueous solution. In addition, some organic solvents, such as isopropanol, can be used. The skilled person will be able to choose a suitable solvent on the basis of his normal knowledge. Depending on the particle size of the powder, it may be desirable to prepare a colloidal solution of the powder, for instance by addition of a base, salt and/or surfactant. When the powder is applied in dispersed form, preferably a drying step takes place each time before a next layer is applied.

According to a preferred embodiment of the invention, in each layer, several materials, of a different nature, are used. It is also possible, and highly favorable under certain circumstances, to modify the composition of the powder per layer to be applied. If per layer one type of material is applied, often a doctor blade (slurry) or counter rotating roller (dry powder) is used. If per layer more than one type of material is applied, this is applied locally, preferably by means of one or more computer-controlled nozzles capable of applying one or several materials. The materials can differ from each other in color or in properties. To be considered here are, for instance, (di)electric or piezoelectric properties. According to this embodiment, the material is preferably applied in the form of a slurry.

According to the invention, different kinds of materials, in particular both ceramic materials and metals, can be used. To be able to properly apply the material to the binder, the material is preferably in powder form. Depending on the size of the powder particles, the powder will be applied in dry form or in dispersed form (slurry). A finer powder leads to a greater accuracy in achieving the desired shape of the dental element. Preferably, the powder has an average particle size (diameter) between 1 nm and 50 $\mu$l, more preferably smaller than 50 nm, still more preferably between 10 nm and 25 nm. The advantage of this is that sintering can be carried out in a short time and at a relatively low temperature. It has been found that the particle size referred to has a positive effect on the shape and sinterability of the dental element to be formed.

The powder can be made of any material that is conventionally used for forming dental elements. For this purpose, in particular metals and ceramic materials and combinations thereof are suitable.

When a ceramic material is used for forming the dental element, this is preferably selected from the group of $SiO_2$, $Al_2O_3$, $K_2O$, $Na_2O$, CaO, $Ba_2O$, $CrO_2$, $TiO_2$, BaO, $CeO_2$, $La_2O_3$, MgO, ZnO, $Li_2O$ and combinations thereof. Optionally, ceramic compositions can further contain F or $P_2O_5$. Particularly suitable ceramic materials are the commercially available compositions. VITADUR®, IPS EMPRESS®, DICOR®, IPS EMPRESS II®, CERESTONE®, CEREPHARAL®, and IN-CERAM®.

When a metal is used for forming the dental element, this is preferably selected from the group of alloys of gold, platinum, palladium, nickel, chromium, iron, aluminum, molybdenum, beryllium, copper, magnesium cobalt and tin. Optionally, such an alloy can contain silicon. For a description of suitable alloys, reference is made to J. P. Moffa, Alternatives to Gold Alloys in Dentistry, DHEW Publication N. (NIH), 77–1227.

If desired, a lubricant can be added to the powder to facilitate applying the powder in layers. Examples of suitable lubricants are stearic acid or derived stearates, such as zinc or calcium stearate. A lubricant is preferably used in an amount of 1–2% by weight, based on the weight of the powder.

As mentioned, preferably, in alternation a layer of binder is applied and a layer of powder is applied thereto. The thickness of the layers of powder is preferably between 0.01 and 0.3 mm, more preferably between 20 and 100 µm, which is beneficial to the surface quality in the case of slight differences in height contour of the layers. The amount of binder per unit area of powder is fairly critical, but can simply be adjusted by a skilled person to the nature of the binder and powder used. Normally, the amount of binder will be between 0.005 and 0.3 grams per square centimeter of powder. Thus, layer by layer the desired dental element is built up.

When the last layer has been applied, excess powder which has not been bound is removed. This can be done by taking out the entire powder bed, turning it upside down and shaking gently. Residues can be removed by blowing, for instance with compressed ir. Thereafter the powder particles can be bonded together by sintering. Preferably, prior to sintering, a debinding step is carried out, i.e., a treatment to remove the binder. Debinding can be carried out by means of heat or a suitable solvent, such as hexane. Because most binders have a relatively complex composition, debinding preferably takes place by heating using a temperature path (for instance from 20 to 500° C.). Such a heating scheme can be simply coupled to a sintering step.

The duration and temperature at which sintering takes place will depend on the nature of the binder used and the powder. Normally, the duration of sintering will be between 10 minutes and 3 hours, while the temperature will typically be between 400 and 800° C. By sintering in such a way that only necks are formed, shrinkage due to the sintering step is minimal/negligible. Optionally, such shrinkage can be compensated by scaling the CAD model.

After sintering, the product obtained is preferably infiltrated, whereby a second phase is introduced into the product. As a result, the porosity of the product is considerably reduced. Densities in excess of 99% are feasible. The infiltration can be ed out, for instance, in an oven, whereby the infiltration material is laid against the dental element. The infiltration material melts at a lower temperature than the material of the dental element. Through capillary action, the liquid infiltration material is infused (adsorbed). This step lasts a relatively short time and gives the dental element the desired properties. A suitable material or this is, for instance, glass-ceramic or a polymer. Preferably, a material is used which has been approved for use in dental elements, as described in the standard ADA no. 15 ANSY MD156.15-1962, which is to be understood to be inserted herein.

In particular cases, it has been found to be advantageous to subject the dental element to a thermal/chemical post-treatment, so that all optimum material (micro)structure is achieved. Thus, preferably, the dental element is briefly heated to a temperature between 60 and 150° C., more preferably between 80 and 130° C.

Instead thereof, or supplemental thereto, preferably a thermal compaction is accomplished. To that end, the dental element is heated to a temperature of at least 250° C., preferably at least 400° C. and more preferably at least 500° C. This treatment contributes to the dental element obtaining particularly favorable properties.

When by one of the procedures described above the dental element has been formed, it may happen that it still needs to be additionally shaped to some extent. As has already been indicated, it is an advantage of the invention that it enables work to be done very accurately. Additional shaping will therefore be less laborious than in the techniques used heretofore. Ways in which additional shaping can be carried out include inter alia grinding, filing, polishing, sanding, blasting or treatment with a ball bed, depending on the selected material of the dental element.

The invention will presently be elucidated in and by the following examples.

Example 1

Two binders were prepared, having the following compositions:

| A: | |
|---|---|
| polyvinyl acetate (Optapix PA 4 G) | 2 wt. % |
| alcohol content (ethanol) | 36 wt. % |
| glycol | 2 wt. % |
| water | balance |
| B: | |
| polyvinyl acetate (Optapix PA 4 G) | 2 wt. % |
| alcohol content (ethanol) | 34 wt. % |
| glycol | 1 wt. % |
| water | balance. |

The compositions were prepared by manually adding the ingredients and stirring. Dissolving the polyvinyl acetate took 6 to 10 hours. Through the alcohol content, the surface tension could be set (a low surface tension proved favorable).

Example 2

With a bindjet printer (Z402 of the firm Z Corporation, Burlington Mass. USA) two cylinders were fabricated, using aluminum powder (type CT 3000SG) in combination with, successively, binder A and binder B (see Example 1). The properties of the powder are as follows:

TABLE 1

| Chemical purity (% by weight) | |
|---|---|
| $Al_2O_3$ | >=99.7 |
| $Na_2O$ | 0.09 |
| $SiO_2$ | 0.02 |
| $Fe_2O_3$ | 0.02 |
| CaO | 0.02 |
| MgO | 0.10 |

Physical properties of the powder:
Specific surface energy range BET: 5.5 to 7.5 m²/g
Median particle size (MPS) d50: 0.5 to 0.7 µm Cilas 850
Particle size d90: 1.0 to 2.0 µm Cilas 850
Ceramic properties of the powder:
Green density: 2.22 g/cm³
Sintered density: 3.90 g/cm³
Shrinkage: 16.5%

The alumina powder is distributed homogeneously over the building platform by means of a divider (kind of razor blade/snow shovel/doctor blade). Thereafter, the layer of loose powder applied is compacted with a coated roller (teflon roller with polyester top layer), so that a smooth and flat layer of loose powder is formed (like flattened castor sugar). Through this compaction step, the initial porosity is rendered substantially lower, which is beneficial to the so-called green strength. The layer thickness of this powder layer is adjustable and has been set at 0.0625 mm (the size of this step determines the accuracy of following the product contours, and may be still smaller).

After the entire building surface has been provided with a new compacted powder layer, binder is locally applied to the loose powder by means of a binder jet printer (Z402 of the firm Z Corp., see also WO-A-97/26802). The location where the binder substance is to be printed has been determined beforehand by software. The binder penetrates so deeply into the loose powder that the powder particles in the new layer are bound to each other and that further the new layer is bonded to the preceding one.

With the cartridge and binder substance used, an optimum in binder amount has been found to be 10× printing per 100 g. The amount of binder at a given layer thickness is 0.0017 g/cm$^2$ per inkjet run. Accordingly, at 10× ink jetting this is 0.017 g/cm$^2$, which leads to a good consistency of the products (they can be handled).

By repeating the recoating and inkjet steps, eventually the entire product is built up in the green (=with binder) form.

The cylindrical products which have been produced had a diameter of 16.4 mm and a height of 18 mm; the mass is 5.3 g. The experiments were carried out in triplicate. The porosity of the alumina cylinders is 45% at a maximum (in the absence of compacting). Compacting leads to a lower porosity (estimate 55–70%).

The intermediate products were subsequently subjected to debinding and sintering according to a specific temperature-time path, whereby heating was done at a rate of 120° C. per hour to a temperature of 1200° C. This temperature was maintained for 120 minutes, followed by cooling to room temperature, again at a rate of 120° C. per hour. The sintered products were subsequently infiltrated with a glass ceramic to obtain the eventual strength and mechanical properties. The obtained properties satisfy the standard imposed on the functional dental elements.

What is claimed is:

1. A method for fabricating a functional dental element using a three-dimensional printing technique comprising:
    applying successive layers of powder onto each other to form the dental element;
    bonding the layers by means of a binder wherein each layer is bonded at desired positions to a preceding layer thereby allowing removal of excess non-adhering material;
    sintering the dental element to form necks between the powder particles;
    and subjecting the sintered dental element to infiltration by second phase.

2. A method according to claim 1, wherein the sintering step is preceded by a debinding step.

3. A method according to claim 1, wherein the shape and dimensions of the dental element are measured in a patient using an optical scan technique.

4. A method according to claim 3, wherein the optical scan technique is a laser technique.

5. A method according to claim 4, wherein the laser technique yields data about shape and dimensions in electronic form.

6. A method according to claim 1, wherein a computer is used for controlling, on the basis of the data obtained upon measuring, a print head which applies the binder to specific, desired positions.

7. A method according to claim 1, wherein the binder is selected from the group consisting of colloidal silica, polyvinyl acetate (PVA), starch adhesives, acrylates, polyvinyl alcohol, polyethylene oxide (PEO), ethylenevinyl acetate (EVA) and derivatives thereof.

8. A method according to claim 1, wherein the powder is a ceramic material, a metal, or a combination of metals and ceramic materials.

9. A method according to claim 8, wherein the ceramic material is selected from the group consisting of $SiO_2$, $Al_2O_3$, $K_2O$, $Na_2O$, $CaO$, $Ba_2O$, $CrO_2$, $TiO_2$, $BaO$, $CeO_2$, $La_2O_3$, $MgO$, $ZnO$, $Li_2O$ and combinations thereof.

10. A method according to claim 8, wherein the metal is selected from the group consisting of alloys of gold, platinum, palladium, nickel, chromium, iron, aluminum, molybdenum, beryllium, copper, magnesium, cobalt and tin and combinations thereof.

11. A method according to claim 1, wherein the layers are applied with a doctor blade.

12. A method according to claim 1, wherein the powder is applied in dispersed form.

13. A method according to claim 12, wherein in a layer, the powder comprises powders of different materials.

14. A method according to claim 13, wherein in a layer, the powder comprises powders of different colors.

15. A method according to claim 12, wherein at least one layer differs in composition from the other layers.

16. A method according to claim 13, wherein the powder is locally applied with a computer-controlled nozzle.

17. A method according to claim 13, wherein at least one of the powders has an average particle size less than 50 nm.

18. A method according to claim 1, wherein the dental element is sintered at a temperature of 400–800° C. for a period between 10 minutes and 3 hours.

19. A method according to claim 1, wherein said infiltration is carried out with a glass-ceramic or a polymer material.

20. A method according to claim 1, wherein the dental element is further shaped by grinding, filing, polishing, sanding, blasting or treatment with a ball bed.

* * * * *